United States Patent [19]

Wortzman

[11] Patent Number: 4,822,600

[45] Date of Patent: Apr. 18, 1989

[54] INFRARED BLOCKER

[75] Inventor: Mitchell S. Wortzman, Los Angeles, Calif.

[73] Assignee: Neutrogena Corporation, Los Angeles, Calif.

[21] Appl. No.: 54,438

[22] Filed: May 27, 1987

[51] Int. Cl.⁴ .................. A61K 7/40; A61K 7/42; A61K 7/44

[52] U.S. Cl. .................... 424/59; 424/60; 514/844; 514/937; 514/938; 514/947; 514/949

[58] Field of Search ............... 514/947, 949; 424/60, 424/59

[56] References Cited

U.S. PATENT DOCUMENTS 4,119,712 10/1978 Goldner et al. .................. 424/63
4,514,383 4/1985 Murray et al. .................. 424/60

Primary Examiner—Dale R. Ore
Attorney, Agent, or Firm—Richard R. Mybeck

[57] ABSTRACT

A transparent or translucent composition for topical application to mammalian skin for protection from infrared rays comprising fumed silica admixed with conventional UV blockers as its principal active constituents.

8 Claims, No Drawings

INFRARED BLOCKER

INTRODUCTION

The present invention relates generally to infrared blocking and more particularly to a new and improved translucent or transparent composition which when applied topically to exposed human skin is surprisingly effective in blocking infrared from the sun and thereby substantially reduces the skin damage which results from exposure to unblocked infrared without creating the ludicrous appearance caused by those blockers containing metallic opaquers.

BACKGROUND OF THE INVENTION

During the past two decades, infrared radiation has received much less attention than ultraviolet with respect to its cutaneous effects. Infrared photons (appreciated by the average human as a sensation of heat) are of relatively low energy. Hence, it has been stated that the inability to start photochemical reactions mitigates infrared's possible contributions to cutaneous carcinogenesis. Only recently has it been suspected that this old view might be fallacious since biochemical reactions are heat-dependent:

$-DG° = RT$ in K (where DG is the standard free energy, R is the gas constant and K is the equilibrium constant).

It is now believed that the infrared/heat axis may contribute to aging and carcinogenesis by amplifying ultraviolet injury, altering the vasculature, producing diffusible mediators, changing histone binding properties, and/or damaging DNA repair processes. (See: Kaidbey, et al, *Arch. Dermatol.*, 1982; 118 (5):315–318.)

Present sunscreens protect against ultraviolet UVB and UVA. Unfortunately, they are no more effective than most types of glass at absorbing infrared radiation. (See: O'Brien, J. P., *Austral J. Dermatol.*, 1980; 21: 1–9.) Infrared rays penetrate deeper than UV rays, and, once absorbed, propagate heat further by conduction and convection. (See: O'Brien, J.P., *Arch. Dermatol.*, 1975; 111: 460–466.) Therefore, present sunscreens leave the skin naked to the atmospherically transmitted infrared radiation. Absorbance and reflectance data have been generated for human skin both white and black, over the 0.4 to 1.6 m (micron) range. The reflectance curves above 1.2 m for differently pigmented persons are practically identical and reflect primarily the absorption spectrum of water. In the spectral range 0.4 m, the reflectance is usually between 50%–70% (the absorbance decreasing as the reflectance increases, indicating relative translucency). Between 0.7 and 2.6 m, water causes prominent absorption bands. This results in reflectance of only 10% from 1.4 m out to 2.6 m. These values are pertinent, especially in high atmospheric transmission wavelengths. (See: Jaquez, J. A. et al., *J. Appl. Physiol.*, 1955; 8: 297–299; and Kuppenheim, H. F. et al., *J. Appl. Physiol.*, 1955; 9: 75–78.)

Principal considerations for selecting effective sunscreens include burning, tanning, and chronic changes such as, cancer, elastosis, wrinkling, telangiectasias and pigmentary mottling. When considering the need for infrared protection, however, little information is available.

Some conditions exist which appear to be associated "purely" with heat or infrared radiation, such as, cutis laxa, that is wizened skin of certain glass blowers, kitchen workers, bakers working with space heating devices (whose biopsies show elastosis); "Glass makers" cataract; Kang cancer of northern China (induced by sleeping on hot bricks); Kangri cancer of India (induced by wearing coal burning pots); Kairo cancer of Japan (from wearing benzene burning flasks); Peat fire cancer of Irish women; and basal cell tumors of cheeks induced by the solar focusing of rimless glasses.

Other diseases associated with infrared exposure include temporal arteritis and actinic granuloma. (See: O'Brien, op cit; and Shabrad, P. et al., *Br. J. Dermatol.*, 1977; 97: 179–186.) In many of these entities, the cutaneous malignancies were found among the clinical changes of erythema ag igne. According to Kligman "whether heat reaches the skin by conduction (i.e., hot bricks, heating pads) or by radiation (i.e., open fires, space heaters), the changes are quite similar. Cancers and erythema ab igne can be produced by either route. (See: "Reflections on Heat", *Br. J. Dermatol,* 1984; 110: 369–355.) The possibility of erythema ab igne being a marker for infrared damage and a predictor for later skin cancers is recognized.

Histologically, similarities between chronic actinic damage and erythema ab igne from non-burning infrared include: early elastic fiber proliferation, increased dermal mast cells, telangiectasia, epidermal dysplasia, and atypia, and irregular melanin distribution. Dissimilarities include greater dermal melanin or hemosiderin deposition and less end-stage degenerative elastosis found in erythema ab igne. The mild upper dermal elastosis of erythema ab igne is superficial. This elastotic material histochemically approximates hyaluronic acid. Epidermal changes of erythema ab igne include atypia amounting to preneoplatic change and basal cell vacuolization. These effects may possibly be caused by infrared radiation, since heat has been shown to cause: cellular respiratory inhibition; decreased DNA, RNA, and protein macromolecular synthesis; increased cellular membrane permeability; decreased nucleolar-cytoplasmic transport of ribosomal RNA; and $G_2$ cell cycle phase accumulations.

Actinic elastosis has been claimed "the chief component if not the basis of aging in sun exposed skin. Also, elastosis is more prominent on biopsy than is clinically apparent." Since elastosis may be unsightly (yellow, wrinkles), preventing infrared or ultraviolet induced elastosis would be a major benefit.

At present, no direct clinical studies adequately separate solar elastosis into ultraviolet versus infrared components, and their respective proportions in humans. Finlayson's work on erythema ab igne indicates only that infrared radiation can cause elastosis in humans. (See: "Erythema ab igne: A histopathological study". *J. Invest. Dermatol.*, 1966; 46: 104–108.) Kligman showed, using guinea pigs, that ultraviolet radiation, alone, produced more numerous, thicker, twisted elastic fibers. Physiologic range infrared radiation, alone, produced numerous fine, feather-like fibers. Infrared and ultraviolet radiations simultaneously produced dense mat-like fibers and increased ground substance that exceeded the sole product of either radiation alone.

The argument has been made that actinic elastosis can be minimized by the use of present ultraviolet sunscreens. An opposing opinion was presented by Pearse, who implied that ultraviolet protection does not insure against chronic sun damage. Some believe that solar elastosis is the result of damaged fibroblasts secreting defective proteins. Infrared radiation has been shown to alter some cellular proteins (enzymes). Further studies are required to determine if infrared radiation affects enzymes or other proteins necessary to the manufacture of elastin.

A dramatic example of solar elastosis may effect the temporal arteries. A study by O'Brien (Op. cit.) reported that the outermost side of temporal arteries possesses the actinic damage similar in severity to exposed skin. Theoretically, only infrared radiation should penetrate to this depth.

Perhaps a better way to separate ultraviolet and infrared effects is through study of the black patient. The black individual, in comparison with the white, is relatively ultraviolet A and B resistant. Black skin, however, has greater infrared and visible radiation absorption. Kligman and Kligman believe that "much of the elastosis in blacks is due to infrared radiation alone." This should be tempered by the fact that, of all racial groups, blacks have the least (highest resistance to) elastosis.

A unique line of reasoning implicates infrared radiation as the cause of actinic granuloma. Nigerians have a 1.7% prevalence of extremely rare granuloma multiforme, the Nigerian equivalent of actinic granuloma. Alledgedly, these Nigerians differ from other blacks because they are exposed to much domestic fire radiation. Therefore, fire exposure, providing infrared radiation and convection heat, is implicated as a cause of actinic granuloma, an elastolytic condition.

The study of the individual effects of infrared or ultraviolet radiation alone may have scholarly merit; but the combination of ultraviolet and infrared radiation may have the greatest effects. Again, heat has been shown to decrease DNA repair after ionizing radiation.

In a more applicable vein, ultraviolet and heat have been shown to synergistically denature human squamous buccal mucosal DNA. This work was carried out at 24° C., 32° C. (representing the temperature of indoor surface skin), and 42° C. (representing the surface skin temperature in bright sunlight at 26° North latitude). (See: Roth and London: *J. Investigative Dermatology;* 69, 368–372; 1977.) Roth et al showed a positive linear relationship between DNA denaturation and irradiation temperature.

In a classic study, Freeman and Knox (See: *Archives of Dermatology;* 89, 858–64; 1964) showed that acute, as well as chronic, combined ultraviolet and infrared exposures may have deleterious effects on mouse skin. The mouse acute-ultraviolet-burn-death-rate rose with temperature. The greatest percentages of mouse cutaneous tumors resulted from ultraviolet exposure and continuous heat as opposed to all other groups to be mentioned. Heat, delivered for three hours following a daily ultraviolet dose, resulted in a greater tumor yield than heat delivered in the immediate three hours prior to the ultraviolet treatment. All of the aforementioned tumor yields were greater than in mice given ultraviolet therapy without exogenous heat.

While more studies may be considered necessary such as, for example, the monitoring of subjects located in variable latitudes and insolation, for both ultraviolet and infrared in regard to chronic deleterious solar effects, and biopsied, assessing one variable (i.e., infrared or ultraviolet) while holding the others constant to assess relative effects, there is sufficient evidence to give reasonable men concern that infrared is the source of deleterious cutaneous effects in man and to inspire efforts toward the development of topical preparations which can provide more than a modicum of protection of the human animal, irrespective of race or pigmentation.

BRIEF SUMMARY OF THE INVENTION

The present invention is predicated upon the surprising discovery of a novel and unique composition of matter containing, inter alia, fumed silica admixed with traditional ultraviolet (UV) absorbers but not opaquers which has the unexpected ability, when applied to mammalian skin, to disperse and block infrared radiation directed thereat and protect the skin from the severe adverse effects thereof.

Accordingly, a prime object of the present invention is to provide a new and improved composition which, when topically applied to human skin provides a blocking action sufficient to reduce the skin damage which would otherwise result from exposure to unblocked infrared radiation.

A further object of the present invention is to provide a new and improved topically applied infrared blocker which is easy to apply, cosmetically acceptable, and has no adverse effect on clothing worn therewith.

Still another object of the present invention is to provide means and methods of protecting the skin of human and like susceptible animals from exposure to infrared radiation with a transparent or translucent substance which imparts no abnormal coloration to the skin.

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

The present invention is directed to an infrared blocker for topical application to the skin of humans and like susceptible animals to deter and prevent infrared radiation from causing dermal destruction and cancer. The present invention also embraces methods of inhibiting the action of infrared on mammalian skin by applying such infrared blocking compositions to such skin.

An important ingredient in the composition of the present invention is fumed silica having an average primary particle size in the range of from about 7 to about 16 millimicrons and containing from about 98.3% to about 99.9% silicon dioxide ($SiO_2$), less than 0.5% alumina ($Al_2O_3$), less than 0.003% ferric oxide ($Fe_2O_3$), less than 0.03% titanium dioxide ($Ti_2$) and less than 0.025% hydrogen chloride (HCl). Suitable reagent is available under the brand name AEROSIL ® grade designations 200, 300 and 972 (Degussa Corporation, Teterborg, N.J.). AEROSIL ® 200 and 300 are preferred because, as will appear, they are capable of blocking over 50% IR irrespective of the base employed whereas Aerosil 972 obtains only about 40% IR blocking even when employed in the preferred base composition.

The compositions of the present invention contain fumed silica or a combination of fumed silica with a mixture of conventional ultraviolet screens or absorbers (but not opaquers) and a pharmaceutically extending medium such as a carrier or vehicle which adapts said agents for application to the skin. Those compositions can be in either solid, liquid, gel, or aerosol form. The active agents of the present invention can also be incorporated into various cosmetic and personal care products such as hand and body lotions, oils, ointments, lip balm products, facial cosmetics and the like.

The amount of fumed silica present in the compositions or the cosmetic and personal care products of this invention may vary greatly but is preferable in a range of about 1 to 10% by weight of the total composition. One or more other agents may be utilized with the fumed silica so that the concentration of the combined agents will preferably be in the range of from 1 to 30% by weight of the composition. Greater amounts of these other agents may be incorporated into various products limited only by processing and economic considerations.

Such other agents or constituents which may be present in the composition of the present invention include water; lanolin; vaseline; glycerol; triglycerides of fatty acids; polyethylene glycols; oxyethyleneated fatty alcohols; esters such as isopropyl palmitate; isopropyl myristate and isopropyl stearate; silicone oils; oleyl oleate and butyl stearate; animal, vegetable and mineral oils; fatty alcohols; glycerol monostearate; and organic and mineral waxes. These other constituents are generally used in an amount of about 10 to 99% by weight of the total formulation.

Among the cosmetic ingredients which may also be used are: thickeners, softeners, superfatting agents, waterproofing agents, emollients, wetting agents and surface active agents, as well as preservatives, anti-foam agents, perfumes or any other compatible ingredient usually employed in cosmetics.

Among the solvents acceptable for use herein are water, lower monoalcohols as well as their mixtures, or aqueous-alcoholic or oil/alcohol solutions, the preferred alcohols being chosen from ethanol, isopropyl alcohol, propylene glycol, glycerol and sorbitol, and the preferred aqueous-alcoholic mixtures being mixtures of water and ethyl alcohol.

The following film-forming agents and cosmetic resins are also useful in the practice of the present invention, namely: polyvinylpyrrolidone; vinylpyrrolidone/vinyl acetate copolymers in which the monomers ratios are from 70/30 to 30/70; vinyl acetate/unsaturated carboxylic acid copolymers such as a copolymer containing 90% of vinyl acetate and 10% of crotonic acid, terpolymers of methyl methacrylate/stearyl methacrylate/dimethylaminoethyl methacrylate, completely quaternised with dimethyl sulphate, the monomers being used particularly in the ratio 20/23/57, and a terpolymer of vinyl acetate/allyl stearate/allyloxyacetic acid, especially in the ratio of 80/15/5, maleic anhydride/methyl vinyl ether copolymers such as those commercially referred to as "Gantrex AN" as well as the ethyl, isopropyl and butyl esters of these copolymers, and maleic anhydride/butyl vinyl ether copolymers.

Sunscreen compositions now generally available are formulated in the form of creams, gels, lotions and oils containing as the active agents ultraviolet light absorbing chemical compounds. The active chemical compounds act to block the passage of erythemogenic radiation, by absorption, thereby preventing its penetration into the skin.

For topical application, sunscreen compositions must be non-toxic and non-irritating to the skin tissue and capable of application to the skin as a uniform continuous film. In addition, the active sunscreening agents must be chemically stable and in particular must be resistant to chemical and photodegradation when on the skin as well as resistant to absorption through the skin. Among the widely used ultraviolet absorbing agents meeting the aforesaid conditions are: oxybenzone(2-hydroxy-4-methoxybenzophenone); dioxybenzone(2,2'-dihydroxy-4-methoxybenzophenone); amino benzoic acid; cinoxate(2-ethoxyethyl-p-methoxycinnamate); diethanolamine-p-methoxycinnamate; digalloyl trioleate ethyl 4-bis(hydroxypropyl)aminobenzoate; 2-ethylhexyl-2-cyano-3,3-diphenylacrylate; ethylhexyl-p-methoxycinnamate; 2-ethylhexyl salicylate; glyceryl aminobenzoate; homosalate(3,3,5-trimethylcyclohexyl salicylate); triethanolamine salicylate; 2-phenylbenzimidazole-5-sulfonic acid; sulisobenzone(2-hydroxy-4-methoxybenzophenone-5-sulfonic acid); Padimate A (amyl p-dimethylaminobenzoate); Padimate 0 (octyl dimethyl para aminobenzoate); 4-t-butyl-4'-methoxydibenzoylmethane; the combination of 2-hydroxy-1,4-naphthoquinone with dihydroxyacetone; and menthyl anthranilate.

Each of the foregoing compounds have been used alone or in combination in various sunscreen compositions and been found to provide varying sun protection factors (SPF) when evaluated in human subject utilizing standard solar simulator tests.

The sunscreen material for ultraviolet-A (320–400 nm) is selected from the group comprising the pentyl and 2-ethylhexylesters of 4-(dimethylamino)benzoic acid; dioxybenzone; ethylhexyl-p-methoxy-cinnamate; ethyl 4-bis(hydroxypropyl)aminobenzoate; 3,3,5-trimethylcyclohexyl salicylate; 2-ethylhexyl-2-cyano-3,3 diphenylacrylate; 2-ethyl-hexyl salicylate; 4-t-butyl-4'-methoxydibenzoylmethane and mixtures thereof. The sunscreen material is present in amounts ranging from 1.0% to 20.0%, preferably 4.0% to 15.0% by weight of the total composition.

In general, it is advantageous, in a sunscreen agent which contains UV-A filter, additionally to use a filter substance for the UV-B range (290 to 320 nm). Examples of customarily used UV-B absorbers include 2-ethylhexyl p-methoxycinnamate; isoamyl-p-methoxycinnamate; p-methylbenzylidene-D, L-camphor or its sodium sulfonate, sodium 2-phenylbenzimidazole-5-sulfonate, sodium 3,4-dimethylphenylglyoxylate, 4-phenylbenzophenone, isooctyl 4-phenylbenzophenone-2'-carboxylate, p-methoxycinnamate, 2-phenyl-5-methylbenzoxazole, octyl-dimethyl-para amino benzoate, and p-dimethylaminobenzoate and the like.

The ratio of fumed silica to UVA and UVB filters when the filters are desired is generally 1:1 to 1:5.

In one practice of the present invention, a suitably sized stainless steel tank is charged with mineral oil and the dual mixers (the sweep rotating at about 10 RPM clockwise while the turbine rotates at about 12 RPM counterclockwise) are activated. Next a suitable solvent-carrier such as PEG-7 Glyceryl Cocoate is added followed by an oil such as cetearyl isononanoate and an ultraviolet B absorber, such as octyl methoxycinnamate, with continued mixing.

Next, the batch is heated to 78°–80° and, while heating, stearalkonium hectorite and propylene carbonate are added and the mixing is accelerated (sweep at 14 RPM and turbine at 24 RPM) until the gel is completely and homogeneously dispersed.

With the mixers at the speed indicated, an ultraviolet A absorber, such as benzophenone-3, is introduced and completely dissolved into the batch. The mixers are then maintained at the higher speed and the temperature is maintained at 78°-80° C. for one hour.

Added next with stirring is a suitable antioxidant such as dl alpha tocopherol and a suitable cosmetic additive such as cyclomethicone. When these ingredients are completely blended into the batch, it is time to incorporate the fumed silica (AEROSIL ®) with a jet stream mixer (to avoid dust formation) while speeding up the mixers (sweep 14 RPM; turbine 35 RPM) and maintaining the mixing until a homogeneous paste is created.

The batch is then cooled at a rate of about 0.5° C./minute until a temperature of 25°-27° C. is reached. The batch, subject to Quality Control approval is now ready for packaging.

Using the foregoing procedure, compositions embodying the present invention were prepared as shown below:

| Ingredient | W/W percent |
|---|---|
| Mineral Oil | 25.5–88.4 |
| $C_{12-15}$ Alcohol benzoate | 5–30 |
| Octyl methoxycinnamate | 1–7.5 |
| Fumed Silica | 1–8.0 |
| Propylene/carbonate and Stearalkonium hectorite | 1–10 |
| Benzophenone-3 | 1–5 |
| Cyclomethicone | 0.5–3.0 |
| dl-alpha tocopherol | 0.1–1.0 |
| PEG-7 glycerol cocoate | 1–5 |
| Cetearyl Isononanoate | 1–5 |

To further illustrate the present invention, and not by way of limitation, the following examples are presented.

EXAMPLE 1

The materials listed under phase A are placed in a suitably sized vessel and admixed. When these materials are blended to a uniform consistency and composition, the materials listed under Phase B are added to the extant mixture. All of the materials in the vessel are then admixed in the conventional manner. The IR blocker is then added to the mixture and blended throughout. Any additional materials are then added as necessary and blended throughout the mixture.

The mixing time, temperature, and number of phases is, of course, dictated by the particular materials used. All such mixing is done in the conventional manner.

EXAMPLE 2

Using the method of Example 1, the following are combined, by weight percent:

| Phase A | |
|---|---|
| Purified Water USP | 58.5 |
| Glycerine, 96% | 5.0 |
| Methyl Parahydroxybenzoate | .2 |
| DEA Methoxycinnamate | 5.0 |
| Phase B | |
| Hyrogenated Polyisobutene | 3.0 |
| 1-Hexadecanol | 2.5 |
| 1 Octadecanol | 2.5 |
| Cholesterol USP | 1.0 |
| $R(OCH_2CH_2)_n$ OH Where R represents a blend of cetyl and stearyl radicals and n has an average value of 20 | 5.0 |
| Oxybenzone (2-hydroxy-4-methoxybenzophenine) | 3.0 |
| Dimethicone 1000 cps | 5.0 |
| 4-Hydroxybenzoic Acid, Propyl Ester | .01 |
| Phase C | |
| Fumed Silica | 6.0 |
| Phase D | |
| Purified Water USP | 3.0 |
| N',N''—Methylenebis[N'—[1-(Hydroxymethyl)-2,5-Dioxo-4-Imidazolidinyl]Urea] | .3 |

EXAMPLE 3

Using the method of Example 1, the following are combined, by weight percent:

| Phase A | |
|---|---|
| Purified Water USP | 58.5 |
| Glycerol | 4.5 |
| Methyl Parahydroxybenzoate | 0.5 |
| DEA Methoxycinnamate | 4.0 |
| Phase B | |
| Isopropyl stearate | 5.0 |
| 1-Octadecanol | 4.0 |
| Oxybenzone | 4.0 |
| Lanolin | 3.0 |
| Diemethicone 1000 cps | 3.5 |
| Phase C | |
| Fumed silica | 8.0 |
| Phase D | |
| Purified Water USP | 5.0 |

EXAMPLE 4

Using the method of Example 1, the following are combined, by weight percent:

| Phase A | |
|---|---|
| Purified Water USP | 55.5 |
| Lanolin | 5.0 |
| 4-phenyl benzophenone | 3.5 |
| DEA Methoxycinnamate | 4.5 |
| Phase B | |
| 1-Hexadecanol | 3.5 |
| 3,3,5-trimethylcyclohexyl salicylate | 4.5 |
| p dimethyl aminobenzoate | 4.5 |
| Oxybenzone | 3.0 |
| 4-hydroxybenzoic acid, propyl ester | 0.5 |
| Butyl stearate | 5.0 |
| Phase C | |
| Fumed silica | 1.5 |
| Glycerol monostearate | 4.0 |
| Mineral oil | 5.0 |

EXAMPLE 5

Using the method of Example 1, the following are combined, by weight percent:

| Phase A | |
|---|---|
| Purified Water USP | 35.0 |
| Mineral oil | 7.5 |
| Glycerol monostearate | 10.0 |
| Isopropyl myristate | 8.0 |
| Ethanol | 8.0 |
| Phase B | |
| Polyvinyl pyrrolidone | 5.0 |
| Octyl-dimethyl-para amino benzoate | 4.0 |
| p amino benzoic acid | 1.5 |
| glyceryl amino benzoate | 1.0 |
| p dimethylamino benzoate | 3.5 |
| Phase C | |
| Fumed silica | 10.5 |
| Phase D | |
| Isopropyl palmitate | 3.5 |

| | |
|---|---|
| -continued | |
| BHA | 2.5 |

EXAMPLE 6

Using the method of Example 1, the following are combined, by weight percent:

| | |
|---|---|
| Phase A | |
| Purified Water USP | 86.0 |
| Ethanol | 5.0 |
| Phase B | |
| Oxybenzone | 3.0 |
| Phase C | |
| Fumed silica | 4.0 |
| Phase D | |
| p dimethylamino benzoate | 2.0 |

EXAMPLE 7

Using the method of Example 1, the following are combined, by weight percent:

| | |
|---|---|
| Phase A | |
| Lanolin | 20.0 |
| Glycerol | 15.0 |
| Phase B | |
| Glycerol monostearate | 15.0 |
| PABA | 20.0 |
| Mineral oil | 9.0 |
| BHA | 3.0 |
| Oxybenzone | 6.0 |
| Phase C | |
| Fumed silica | 6.0 |
| Phase D | |
| p dimethylamine benzoate | 6.0 |

EXAMPLE 8

In another practices of the present invention, a suitably sized stainless steel tank is charged with mineral oil and the dual mixers (the sweep rotating at about 10 RPM clockwise while the turbine rotates at about 12 RPM counterclockwise) are activated. Next a suitable solvent-carrier such as PEG-7 Glyceryl Cocoate is added followed by an oil such as cetearyl isononanoate and an ultraviolet B absorber, such as octyl methoxycinnamate, with continued mixing.

Next, the batch is heated to 78°–80° and, while heating, stearalkonium hectorite and propylene carbonate are added and the mixing is accelerated (sweep at 14 RPM and turbine at 24 RPM) until the gel is completely and homogeneously dispersed.

With the mixers at the speed indicated, an ultraviolet A absorber, such as benzophenone-3 is introduced and completely dissolved into the batch. The mixers are then maintained at the higher speed and the temperature is maintained at 78°–80° C. for one hour.

Added next with stirring is a suitable antioxidant such as dl alpha tocopherol and a suitable cosmetic additive such as cyclomethicone. When these ingredients are completely blended into the batch, it is time to incorporate the fumed silica (AEROSIL®) with a jet stream mixer (to avoid dust formation) while speeding up the mixers (sweep 14 RPM; turbine 35 RPM) and maintaining the mixing until a homogeneous paste is created.

The batch is then cooled at a rate of about 0.5° C./minute until a temperature of 25°–27° C. is reached. The batch is ready for packaging.

Using the foregoing procedure, compositions embodying the present invention were prepared a shown below:

| Ingredient | W/W percent |
|---|---|
| Mineral Oil | 25.5–88.4 |
| $C_{12-15}$ Alcohol benzoate | 5–30 |
| Octyl methoxycinnamate | 1–7.5 |
| Fumed silica | 1–8.0 |
| Propylene/carbonate and Stearalkonium hectorite | 1–10 |
| Benzophenone-3 | 1–5 |
| Cyclomethicone | 0.5–3.0 |
| dl-alpha tocopherol | 0.1–1.0 |
| PEG-7 glycerol cocoate | 1–5 |
| Cetearyl Isononanoate | 1–5 |

EXAMPLE 9

Using the procedure of Example 8, an anhydrous translucent sun blocker was prepared having the following formula:

| | |
|---|---|
| Mineral Oil | 10–17 |
| Purified Water - USP | 42.9–81 |
| Hydrogenated Castor oil | 3–8 |
| PEG-60 Lanolin | 1–5 |
| $C_{12-15}$ Alcohol benzoate | 1–5 |
| Silica | 1–8 |
| Octyl methoxycinnamate | 1–7.5 |
| Benzophenone 3 | 1–5 |
| Dimethicone | 1–3 |

EXAMPLE 10

Using the procedure of Example 8, a sun blocker emulsion was prepared having the following formula:

| | |
|---|---|
| Purified Water - USP | 57–89.4 |
| Carbomer 934 | .1–.5 |
| Benzophenone 3 | 1–5 |
| Octyl methoxycinnamate | 1–7.5 |
| Propyleneglycol | 1–4 |
| Polysorbate 80 | 1–3 |
| Stearic acid | 1–5 |
| Cetyl Palmitate | 1–2 |
| Glyceryl stearate | 1–2 |
| Cocoa butter | 1–2 |
| Phenyl dimethicone | 1–3 |
| Triethanolamine (85%) | .5–1 |
| Silica | 1–8 |

EXAMPLE 11

Using the procedure of Example 8, a sun blocker emulsion was prepared having the following formula:

| | |
|---|---|
| Purified Water - USP | 52–90.4 |
| Carbomer 934 | .1–.5 |
| Benzophenone 3 | 1–5 |
| Octyl methoxycinnamate | 1–7.5 |
| Polysorbate 80 | 1–5 |
| Stearic acid | 1–5 |
| Cetyl Palmitate | 1–5 |
| Glyceryl stearate and PEG-60 stearate | 1–3 |
| Cetyl Alcohol | 1–5 |
| Cyclomethicone | 1–3 |
| Triethanolamine (85%) | .5–1 |

-continued

| | |
|---|---|
| Silica | 1–8 |

EXAMPLE 12

Using the procedure of Example 8, a sun blocker emulsion was prepared having the following formula:

| | |
|---|---|
| Mineral Oil | 25.5–87.9 |
| $C_{12-15}$ Alcohol benzoate | 5–20 |
| Isopropyl Palmitate | 1–20 |
| PEG-7 glyceryl cocoate | 1–5 |
| Cetearyl Isononanoate | 1–5 |
| Octyl Methoxycinnamate | 1–7.5 |
| Benzophenone 3 | 1–5 |
| Phenyl dimethicone | 1–3 |
| Silica | 1–8 |
| dl alpha tocopherol | .1–1 |

EXAMPLE 13

The sunscreen efficacy of the compositions embodying the present invention was measured with a Cary 14 Double Beam Spectrophotometer in the full IR spectrum, that is, between 700 and 2600 nanometers. The meter was selected because it measures both incident and transmitted energy at any wave length while scanning the spectrum of wave lengths. A slit lamp is used to control the wave length of the transmitted radiation.

In conducting the measurements, a xenon lamp was used as the IR source and a substrate formed of an IR transparent material such as MYLAR ®-D was interposed between the IR source and the meter. Each test composition is dispersed upon the substrate at a concentration of two microliters per square centimeter. The meter permitted a measurement of the percentage of the total infrared blocked by the substrate and is reported in Table A below:

TABLE A

| SPECIMEN | % IR BLOCKED |
|---|---|
| Anhydrous base w/o silica | 1.0 |
| Anhydrous base with silica | 59.8 |
| Base and chemical screen w/o silica | 6.6 |
| Base and chemical screen with silica | 40.0 |
| Base and physical screen w/o silica | 26.5 |
| Base and physical screen with silica | 67.6 |

EXAMPLE 14

Using the measuring technique described in Example 13, a mineral oil base ("M.O") with varying amounts of fumed silica (in weight percent) was measured for blocking and the results are shown in TABLE B.

TABLE B

| Composition | Percent IR Blocked |
|---|---|
| M.O. with 3% silica | 39.7 |
| M.O. with 6% silica | 59.8 |
| M.O. with 8.65% silica | 65.4 |

The foregoing demonstrates the unexpected ability of fumed silica, a non-opaque material, to provide a significant level of infrared protection.

EXAMPLE 15

The procedures of Examples 13 and 14 were repeated using excised mouses skin (obtained from the Skin and Cancer Hospital, Philadelphia, PA) as the substrate instead of the MYLAR ®. The results obtained clearly corroborated with a recognized laboratory equivalent to human skin.

From the foregoing, it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A method of protecting mammalian skin from infrared radiation having a wavelength of between 700 and 2600 nanometers comprising applying to such skin in need thereof a small but effective amount of a composition consisting of from about 1 to about 10 percent by weight of fumed silica and a non-toxic, non-irritating cosmetically acceptable carrier.

2. A method according to claim 1 in which said carrier is an emulsion.

3. A method according to claim 1 in which said carrier is anhydrous solvent.

4. A method according to claim 1 in which said composition contains up to about 20% of UVA and UVB blockers.

5. A method according to claim 2 in which said composition contains up to about 20% of UVA and UVB blockers.

6. A method according to claim 3 in which said composition contains up to about 20% of UVA and UVB blockers.

7. A method according to claim 1 in which said carrier consists essentially of mineral oil.

8. A method according to claim 7 in which said composition contains up to about 20% of UVA and UVB blockers.

* * * * *